United States Patent
Kaneko et al.

(10) Patent No.: US 12,130,047 B2
(45) Date of Patent: Oct. 29, 2024

(54) SAFETY CABINET

(71) Applicant: Hitachi Industrial Equipment Systems Co., Ltd., Tokyo (JP)

(72) Inventors: Takeshi Kaneko, Tokyo (JP); Takeshi Matsumura, Tokyo (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 0 days.

(21) Appl. No.: 17/620,785

(22) PCT Filed: Jun. 17, 2021

(86) PCT No.: PCT/JP2021/023124
§ 371 (c)(1),
(2) Date: Dec. 20, 2021

(87) PCT Pub. No.: WO2022/264388
PCT Pub. Date: Dec. 22, 2022

(65) Prior Publication Data
US 2024/0027079 A1    Jan. 25, 2024

(51) Int. Cl.
*F24F 3/163* (2021.01)
*B01L 1/02* (2006.01)
*B01L 1/04* (2006.01)

(52) U.S. Cl.
CPC ............... *F24F 3/163* (2021.01); *B01L 1/02* (2013.01); *B01L 1/04* (2013.01); *B01L 2300/0858* (2013.01)

(58) Field of Classification Search
CPC .... F24F 3/163; B01L 1/02; B01L 1/04; B01L 2300/0858
USPC .............................................................. 454/57
See application file for complete search history.

(56) References Cited

U.S. PATENT DOCUMENTS

| | | | |
|---|---|---|---|
| 3,000,292 A * | 9/1961 | Wojan | B08B 15/023 D24/234 |
| 3,811,250 A | 5/1974 | Fowler, Jr. | |
| 3,895,570 A * | 7/1975 | Eagleson, Jr. | B08B 15/023 55/DIG. 18 |
| 4,215,627 A * | 8/1980 | Garriss | B08B 15/023 118/DIG. 7 |

(Continued)

FOREIGN PATENT DOCUMENTS

| | | |
|---|---|---|
| JP | 04-105884 A | 4/1992 |
| JP | 2004-031928 A | 1/2004 |

(Continued)

OTHER PUBLICATIONS

Taiwan Office Action issued on Oct. 24, 2022 for Taiwan Patent Application No. 110141819.

*Primary Examiner* — Avinash A Savani
*Assistant Examiner* — Dana K Tighe
(74) *Attorney, Agent, or Firm* — Volpe Koenig

(57) ABSTRACT

A laminar flow at a high air speed can be maintained, and contamination caused by operation of a device or operation of the device by a person can be suppressed as much as possible. There is provided a safety cabinet that supplies clean air into a work room from above, the cabinet including: an opening portion in a front surface of the work room; a front shutter; partition plates provided on right and left side surfaces and a back surface on an upper side of the work room; and a partition on a front upper side of the work room.

7 Claims, 3 Drawing Sheets

(56) References Cited

U.S. PATENT DOCUMENTS

| | | | |
|---|---|---|---|
| 6,632,260 B1* | 10/2003 | Siemers | B08B 15/023 |
| | | | 454/189 |
| 10,350,588 B2 | 7/2019 | Kaneko et al. | |
| 10,384,243 B2* | 8/2019 | Wang | B08B 15/023 |
| 10,843,183 B2* | 11/2020 | Ono | G01N 33/0009 |
| 2013/0090049 A1* | 4/2013 | Meisenzahl | B08B 15/023 |
| | | | 454/56 |
| 2016/0160167 A1 | 6/2016 | Kobayashi et al. | |
| 2020/0149762 A1 | 5/2020 | Ono et al. | |

FOREIGN PATENT DOCUMENTS

| | | |
|---|---|---|
| JP | 2005-156082 A | 6/2005 |
| JP | 2019-074237 A | 5/2019 |
| WO | 2015/046413 A1 | 4/2015 |

* cited by examiner

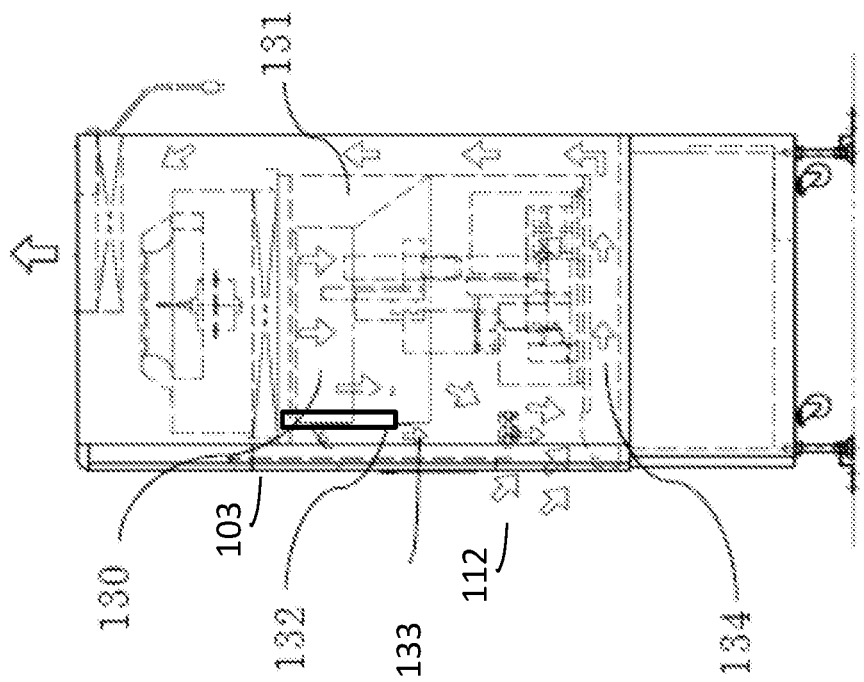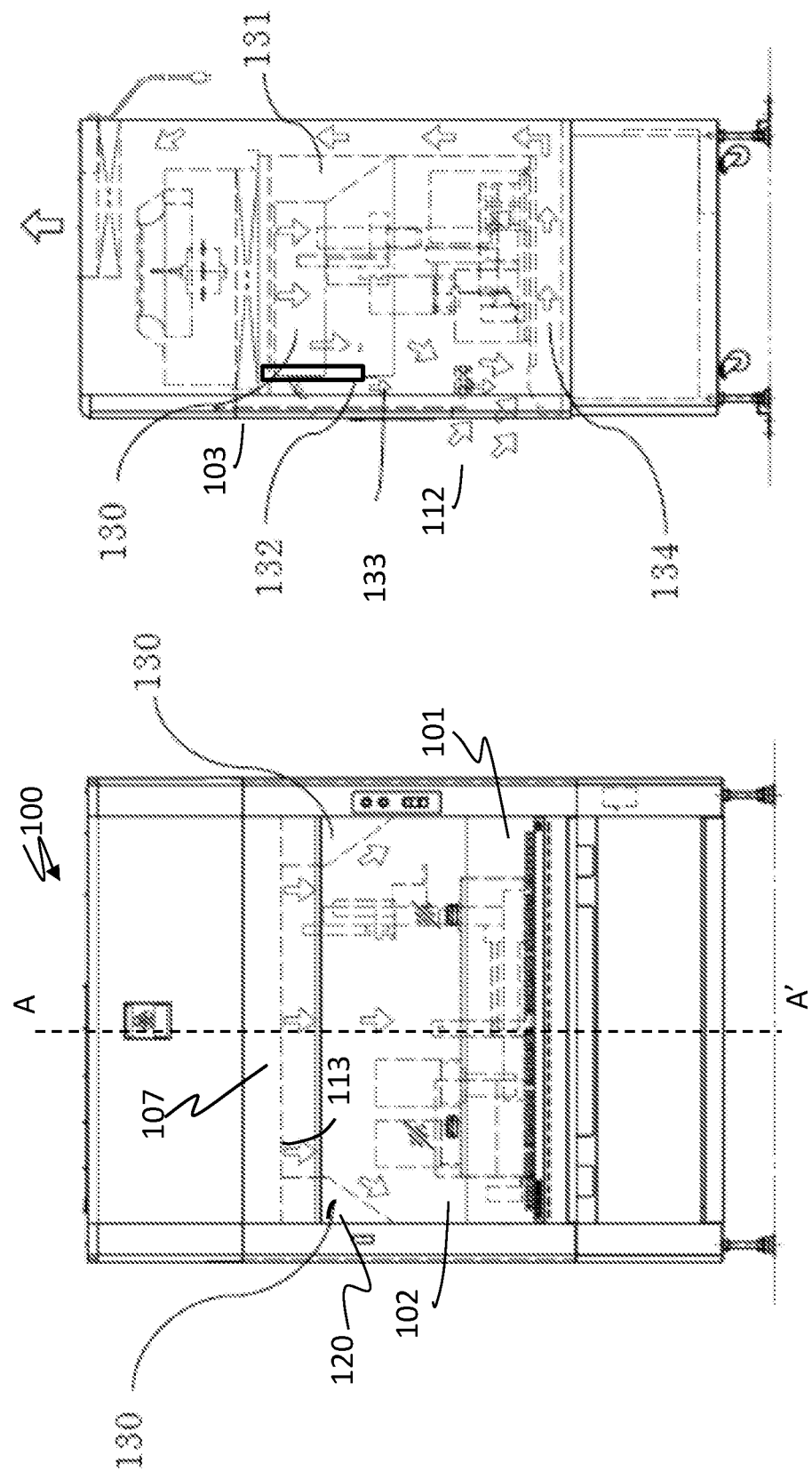

A-A'CROSS SECTION

SAFETY CABINET

TECHNICAL FIELD

The present invention relates to a safety cabinet to be used for regenerative medical treatments, industrial purposes, medicine development, research on pathogens, etc.

BACKGROUND ART

When pathogens, etc. are handled for manipulation and observation of cells, research on pathogens such as viruses, medicine development such as vaccine development, etc., a safety cabinet is to be used.

As one example of the safety cabinet, Patent Document 1 discloses a safety cabinet in which a blowout HEPA filter is provided in an upper portion of a work room, an openable and closable front shutter is provided in a front portion of the work room, a rear grille is provided at a lower rear, and a front grille is provided at a lower front. Then, in the safety cabinet disclosed, air is to be uniformly supplied from the blowout HEPA filter into the work room, and air is to be suctioned from the front grille and the rear grille of a workbench forming a bottom surface of the work room, so that the air flows down from a top to a bottom to clean the work room.

CITATION LIST

Patent Document

Patent Document 1: JP 2019-74237 A

SUMMARY OF THE INVENTION

Problems to be Solved by the Invention

The use of the safety cabinet can prevent contamination caused by manipulation and observation of cells or the handling of pathogens, etc. in the work room, and can prevent a leakage of the pathogens, etc. from inside the work room to a worker side.

In the safety cabinet disclosed in Patent Document 1, a worker sits in front of the safety cabinet, inserts the arms into the work room from a work opening portion below the front shutter, and performs work, and a case is not considered in which a device such as a cell production machine such as a 3D bioprinter or a conveyance machine is to be installed and handled inside the safety cabinet. Namely, a downflow air speed in the entire work room when a device is installed in the work room is not taken into consideration.

An object of the present invention is to provide a safety cabinet that prevents cells, pathogens, etc. from being contaminated when a device such as a cell production machine such as a 3D bioprinter or a conveyance machine is installed inside the safety cabinet.

In addition, an object of the present invention is to provide a safety cabinet capable of preventing cells, pathogens, etc. from leaking to a worker side from inside a work room.

Solutions to Problems

In order to solve the above problem, according to one example of the present invention, there is provided a "safety cabinet" in which a device is to be mounted in a work room, the cabinet including: the work room that retains a negative pressure state formed inside a front shutter; a circulation flow path formed of a lower surface side of the work room, a side surface side of the work room, a back surface side of the work room, and an outer portion of the safety cabinet; and a partition plate that causes a horizontal cross-sectional area of a lower portion of the work room to be wider than a horizontal cross-sectional area of an upper portion of the work room.

In addition, according to another example of the present invention, there is provided a "safety cabinet" that supplies clean air into a work room from above, the cabinet including: an opening portion in a front surface of the work room; a front shutter; and an exhaust slit provided in a workbench on which a device is to be installed, along an outer periphery of the device on a surface of the workbench, the surface adjoining an exhaust circulation flow path below the workbench, and the device to be installed on the surface.

Effects of the Invention

According to the present invention, since the partition plates are provided on the right and left side surfaces and the back surface on the upper side of the work room, a downflow airstream at a high air speed capable of guaranteeing a laminar flow in the work room, for example, equivalent to 0.45 m/s can be retained.

According to the present invention, since the partition is provided on the front upper side of the work room, a downflow airstream at a high air speed capable of guaranteeing a laminar flow in the work room, for example, equivalent to 0.45 m/s can be retained.

In addition, the safety cabinet can be provided that is capable of securing cleanliness without a leakage of dust to the outside, the dust being generated by operation of the device, and that prevents a leakage from inside the work room to a worker side.

Further, a strong air barrier can be formed by clear air on an inner surface on a work room side of the front shutter and two layers of clean air on an inner surface of the partition on the front upper side of the work room, and contamination caused by operation of the device or work by a person can be suppressed.

Tasks, configurations, and effects other than those described above are apparent from the description of the following embodiments.

BRIEF DESCRIPTION OF THE DRAWINGS

FIG. 1A is a front view of a safety cabinet of a first embodiment.

FIG. 1B is a cross-sectional view of the safety cabinet of the first embodiment.

MODE FOR CARRYING OUT THE INVENTION

The flow of airstreams inside a safety cabinet will be described before embodiments of the present invention will be described.

Figure 3B:
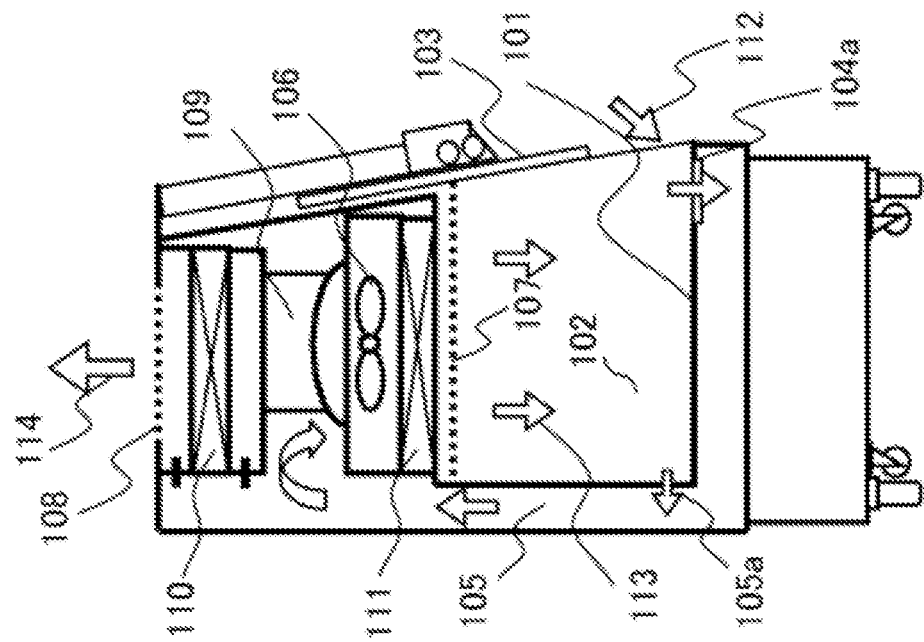
FIG. 3B is a cross-sectional view of the safety cabinet.
Figure 3A:
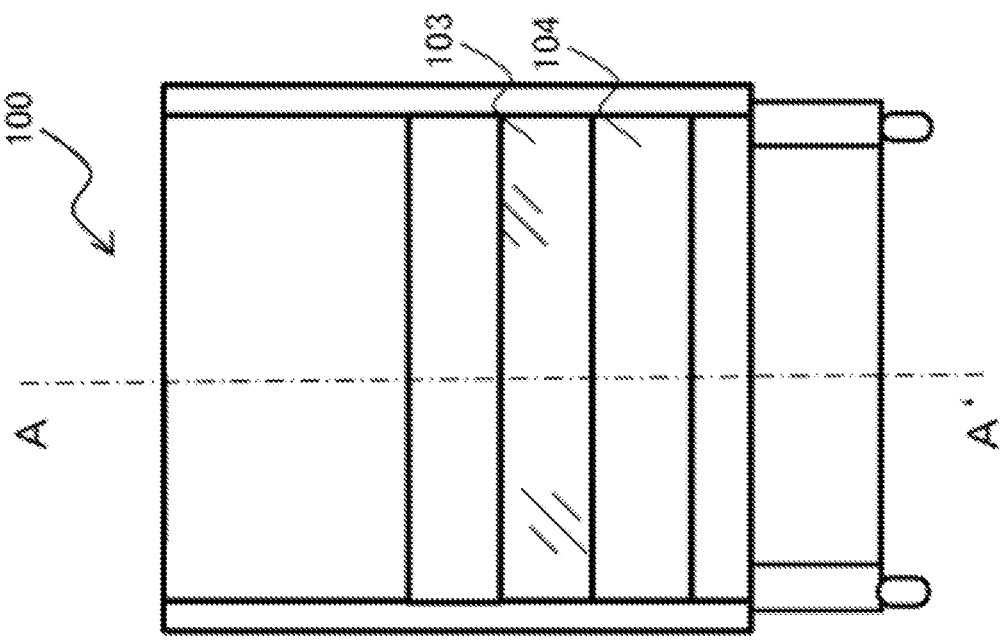
FIG. 3A is a front view of the safety cabinet.

FIG. 3A illustrates a schematic front view of a safety cabinet, and FIG. 3B illustrates a schematic cross-sectional view of the safety cabinet when an A-A' cross section in FIG. 3A is viewed from the left.

The safety cabinet includes various cabinets for regenerative medical treatments, industrial purposes, etc. In the following description, a safety cabinet to be used for medicine development or research on pathogens, etc. will be specifically described.

A work room 102 of which the front surface is formed of a front shutter 103 is disposed inside a safety cabinet 100. The work room 102 retains a negative pressure state formed inside the front shutter. A work opening portion 104 is formed below the front shutter 103, and a worker inserts the arms into the work room 102 from the work opening portion 104, and performs work while seeing the work room 102 through the front shutter 103.

A lower surface of the work room 102 is formed of a workbench 101, and a front slit 104a is disposed on a front shutter 103 side of the workbench 101. When a safety cabinet fan 106 is operated, a pressure chamber 109 is to be pressurized. A blowout HEPA filter 111 is connected to the pressure chamber 109, and dust in the pressure chamber 109 is to be filtered with the blowout HEPA filter 111, and clean air is to be blown out and straightened by a blowout straightening plate 107, and then is to be supplied into the work room 102, as a blowout airstream 113.

An exhaust HEPA filter 110 is also connected to an upper side of the pressure chamber 109. Air pressurized in the pressure chamber 109 is to be filtered with the exhaust HEPA filter 110 and to be exhausted from the safety cabinet 100 through a safety cabinet exhaust port 108, as exhaust air 114.

Air (inlet airstream 112) of an amount equal to the amount of the air exhausted from the safety cabinet 100 (exhaust air 114) enters the safety cabinet 100 from the work opening portion 104 below the front shutter 103. The air is the inlet airstream 112 to be generated in the work opening portion 104 below the front shutter 103. The inlet airstream 112 is to be suctioned into the front slit 104a, together with a part of the blowout airstream 113 in the work room 102. The air passes below the workbench 101. The inlet airstream 112 is to be suctioned from a rear slit 105a formed in a surface of the work room 102 opposite the front shutter 103, together with a part of the blowout airstream 113, and to be suctioned to the safety cabinet fan 106 through a circulation flow path 105. The circulation flow path 105 is formed of a lower surface side of the work room 102, a side surface side of the work room, a back surface side of the work room 102, and an outer portion of the safety cabinet. Namely, the inlet airstream 112 suctioned from the work opening portion 104 circulates through a flow path formed of a lower portion of the workbench 101 (lower surface of the work room 102), side surfaces and a back surface of the work room 102, and a main body portion of the safety cabinet 100. The inlet airstream 112 passing through the circulation flow path 105 is to be suctioned to the safety cabinet fan 106 and to be exhausted from the safety cabinet 100, as the exhaust air 114.

Since dust and aerosols containing pathogens, etc. are handled in the work room 102, the dust and the aerosols containing the pathogens, etc. are also present in the circulation flow path 105 and the pressure chamber 109. The dust and the aerosols are to be removed with the blowout HEPA filter 111 when air is supplied to the work room 102, and with the exhaust HEPA filter 110 when air is exhausted from the safety cabinet 100.

A worker sits in front of the safety cabinet 100, inserts the arms into the work room 102 from the work opening portion 104, and performs work while seeing the work room 102 through the front shutter 103.

In such a safety cabinet, regarding a blowout air speed test to check airstream balance according to Japanese Industrial Standards (JIS) K3800-2009, an air speed test is executed at specified points after removable components inside the cabinet are removed.

In an open system such as the safety cabinet, even when a cell production machine such as a 3D bioprinter, a conveyance machine, etc. is installed in the work room of the safety cabinet, setting the downflow air speed in the work room to a certain value, for example, 0.45 m/s±20% (0.36 to 0.54 m/s) is required.

The safety cabinet fan 106 in the related art alone is not sufficient in capacity in satisfying such a requirement. For this reason, adding an exhaust blower or a large-capacity circulation blower is required, which causes an increase in the size of the safety cabinet. Installing the safety cabinet with an increased size in the existing installation space or carrying the safety cabinet with an increased size into an installation space may not be possible.

In addition, electric power consumption or noise increases, which is not preferable. An increase in electric power consumption does not also correspond to demands of the carbon-free age.

According to the safety cabinet of the present embodiment, when a device such as a cell production machine such as a 3D bioprinter or a conveyance machine is installed, a downflow airstream at a high air speed capable of guaranteeing a laminar flow in the work room can be retained.

In addition, according to the safety cabinet of the present embodiment, cleanliness of portions on the periphery of an installation location of a device to be installed in the work room 102 can be secured.

In addition, according to the safety cabinet of the present embodiment, a leakage from the work room to a worker side can be prevented.

Hereinbelow, embodiments of the present invention will be described with reference to the drawings. Incidentally, in each drawing for describing the embodiments, the same components will be denoted by the same names and reference signs, and repeated descriptions thereof will be omitted.

First Embodiment

FIGS. 1A and 1B illustrate a structure example of the safety cabinet 100 corresponding to a biohazard countermeasure Class II cabinet according to a first embodiment. FIG. 1A is a front view thereof. FIG. 1B is a cross-sectional view of the safety cabinet 100 illustrated in FIG. 1A when A-A' cross section is viewed from the left.

The safety cabinet according to the present embodiment includes an opening portion and a front shutter in a front surface of a work room. Clean air is to be supplied into the work room from above, partition plates are provided on right and left side surfaces and a back surface on an upper side of the work room, and a partition is further provided on a front upper side of the work room.

FIG. 1A illustrates the safety cabinet 100 of the first embodiment of the present invention. The illuminance suitable for work is maintained in the work room 102 by an illumination lamp. In addition, generally, a sterilization lamp is provided in an upper portion of the back surface of the work room 102. The sterilization lamp is to be used to sterilize the work room 102 before and after work in combination with decontamination by wiping with 70% alcohol, etc.

As performance of the safety cabinet 100, the prevention of infection of a worker with bacteria and viruses to be handled thereinside is very important, and the function is obtained by isolating air in the work room 102 and air outside the safety cabinet 100 with the front shutter 103.

The safety cabinet 100 of the first embodiment includes side partition plates 130 on the right and left and a back partition plate 131 on the upper side of the work room.

The side partition plates 130 and the back partition plate 131 are attached in a form where an opening of the blowout straightening plate 107 is suppressed, and restricts a blowout portion for the blowout airstream 113. As a result, with the safety cabinet fan 106 in the related art without a major structural change implemented, the air speed of the blowout airstream 113 increases, and an air speed of 0.45 m/s±20% (0.36 to 0.54 m/s) that is the criteria for the formation of a laminar flow can be retained.

The side partition plates 130 and the back partition plate 131 are inclined outward from a position at approximately 150 mm below the blowout straightening plate 107. The inclination is an inclination where the side surfaces of the work room of the safety cabinet 100 abut the side partition plates 130 and the back partition plate 131 at 120 degrees, and is from approximately 30 degrees to 45 degrees. The heave of the blowout airstream 113 is minimized and the stagnation of the blowout airstream 113 by the inclination of the side partition plates 130 and the back partition plate 131. In the vicinity of the workbench 101, a structure without both the side partition plates 130 and the back partition plate 131 is realized, and an installation space of a device and a work space are secured.

Since it can be assumed that a device to be installed on the workbench 101 have various shapes, the side partition plates 130 and the back partition plate 131 may be configured as an up and down slide type such that an upper space in the work room 102 can be adjusted to a shape according to the device to be installed.

In that case, the side partition plates 130 and the back partition plate 131 are configured to slide up and down by approximately 100 mm to 200 mm. The side partition plates 130 and the back partition plate 131 are configured depending on a machine to be installed in the work room 102, and in light of coping with more machines, it is desirable to adopt a configuration in which an up and down stroke of 50 mm to 300 mm is allowed. Since the side partition plates 130 and the back partition plate 131 slide up and down, the downflow air speed can be maintained while retaining a laminar flow to a portion of the device requiring cleanliness or a work region. Hence, cleanliness can be secured.

The configuration has been described in which the side partition plates 130 and the back partition plate 131 are inclined and slide up and down; however, a mechanism may be provided that adjusts the inclination of the side partition plates 130 and the back partition plate 131. In addition, the side partition plates 130 and the back partition plate 131 have been described as basically linear partition plates, but may be configured with convex curved lines in the work room 102.

Namely, the configuration is such that regarding the horizontal cross-sectional area of the work room 102, owing to partition plates such as the side partition plates 130 and the back partition plate 131, the horizontal cross-sectional area is minimized in the vicinity of an upper portion (blowout straightening plate 107) of the work room 102 and is gradually widened to locations at which the side partition plates 130 and the back partition plate 131 abut the side surfaces of the work room 102.

In addition, since an airstream partition plate 132 is provided on the front upper side of the work room, a high air speed of clean air can be secured in a device installation portion requiring a laminar flow and high cleanliness.

In the safety cabinet 100 of the first embodiment, the airstream partition plate 132 is installed at a predetermined distance, for example, 30 mm to 100 mm from the front shutter 103 in a depth direction of the work room 102. The airstream partition plate 132 is a partition plate that abuts the blowout straightening plate 107, extends downward in the work room 102, and has a length of 300 mm from the blowout straightening plate 107 in a down direction, and partitions an airstream from the blowout straightening plate 107 into the blowout airstream 113 and a front shutter backside airstream 133. The front shutter 103 is attached such that a lower end of the front shutter 103 is located at 200 mm up from the workbench 101. A lower end of the airstream partition plate 132 is located at 250 mm above the lower end of the front shutter 103. In the safety cabinet of the present embodiment, a (distance A) from the workbench 101 to the lower end of the front shutter 103, a (distance B) from the lower end of the front shutter 103 to the lower end of the airstream partition plate 132, and the longitudinal length (distance C) of the airstream partition plate are 200 mm, 250 mm, and 300 mm, respectively. When the distance A, the distance B, and the distance C are set at a ratio of 4:5:6, an air barrier effect of the backside airstream of the airstream partition plate 132 can be promoted, the air speed of the backside airstream being increased, and contamination caused by operation of a conveyance unit of a device or manual work by a person can be suppressed. The ratio of the distances A, B, and C can be adjusted in a range of ±10 to 20% depending on the size of a machine to be installed in the work room 102.

In addition, the airstream partition plate 132 does not raise the front shutter backside airstream 133 on a surface on a work room 102 side of the front shutter 103, and an air speed (0.30 to 0.40 m/s) equivalent to that of a safety cabinet in the related art is maintained. Accordingly, an air barrier formed by the inlet airstream 112 that is stable can be maintained, and airstream balance performance that is airstream containment performance stable comparably to that of the safety cabinet can be maintained. When the air speed of the front shutter backside airstream 133 is too high, a high air speed of downflow airstream directly hits the arms of a worker, so that contamination cannot be suppressed. Since the airstream partition plate 132 is provided, the air speed of the front shutter backside airstream 133 can be set to 0.30 to 0.40 m/s, and contamination can be effectively suppressed.

In addition, owing to the inlet airstream 112 at a high air speed of approximately 0.60 m/s, and a downflow airstream having a high air speed of 0.45 m/s in the work room 102 because of partitioning by the side partition plates 130 and the back partition plate 131, the air speed of the front shutter backside airstream 133 therebetween is suppressed to an air speed of 0.30 to 0.40 m/s lower than an air speed on the periphery thereof. When the inlet airstream 112 and the blowout airstream 113 hit the work room 102 side of the airstream partition plate 132, owing to the Coanda effect, the air barrier effect of the backside airstream of the airstream partition plate 132 can be promoted, of which the air speed is increased, and contamination caused by operation of the conveyance unit of the device or manual work by a person can be suppressed.

Second Embodiment

Figure 2B:
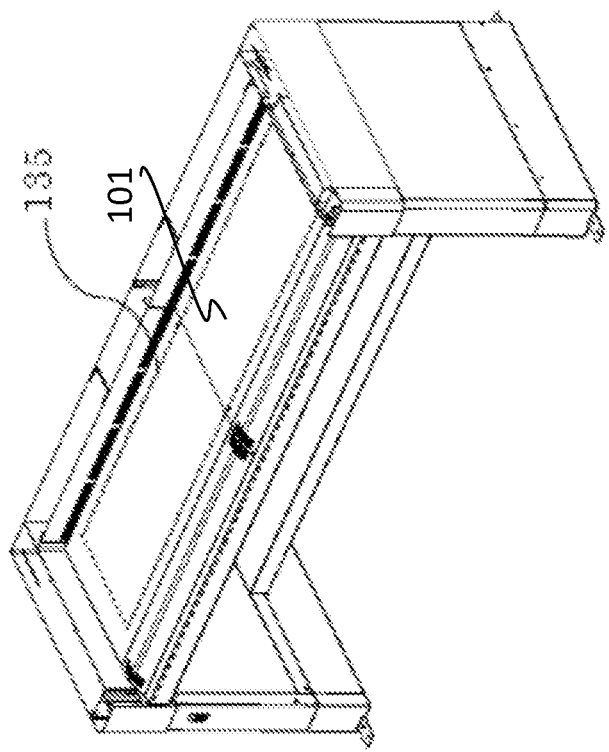
FIG. 2B is a cross-sectional view of the safety cabinet of the second embodiment.
Figure 2A:
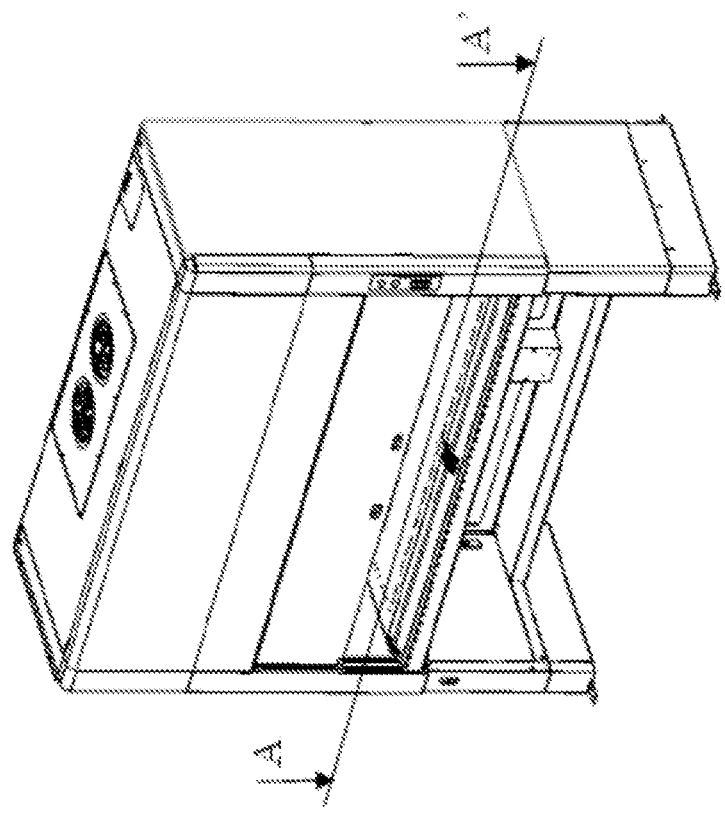
FIG. 2A is a perspective view of a safety cabinet of a second embodiment.

FIGS. 2A and 2B illustrate a safety cabinet of a second embodiment. FIG. 2A is a perspective view of the safety cabinet of the second embodiment. FIG. 2B is a cross-sectional view of the safety cabinet 100 illustrated in FIG. 2A when A-A' cross section is viewed from above.

A plurality of workbench exhaust slits 135 penetrating to an exhaust circulation flow path 134 (refer to FIG. 1B) are provided in the workbench 101 of the safety cabinet of the second embodiment according to an outer periphery of a device to be installed.

The plurality of workbench exhaust slits 135 are provided in the right and left side surfaces and the back surface on the upper side of the work room of the safety cabinet 100, and near the work opening portion 104, namely, in portions on the periphery of a device to be installed on the workbench 101 (peripheral portion of the workbench 101).

Owing to the workbench exhaust slits 135, dust generated when a conveyance unit of the device is operated or when a person operates the device is to be exhausted to the exhaust circulation flow path 134 without stagnation in the work room 102, and to be cleaned with the exhaust HEPA filter 110 (refer to FIG. 3B) or the blowout HEPA filter 111 (refer to FIG. 3B).

REFERENCE SIGNS LIST

100 Safety cabinet
101 Workbench
102 Work room
103 Front shutter
104 Work opening portion
105 Circulation flow path
106 Safety cabinet fan
107 Blowout straightening plate
108 Exhaust port
109 Pressure chamber
110 Exhaust HEPA filter
111 Blowout HEPA filter
112 Inlet airstream
113 Blowout airstream
114 Exhaust air
130 Side partition plate
131 Back partition plate
132 Airstream partition plate
133 Front shutter backside airstream
134 Exhaust circulation flow path
135 Workbench exhaust slit

The invention claimed is:

1. A safety cabinet in which a device is to be mounted in a work room, the safety cabinet comprising:
the work room formed inside a front shutter;
a circulation flow path formed of a lower surface side of the work room, a side surface side of the work room, a back surface side of the work room, and an outer portion of the safety cabinet;
a blowout straightening plate that supplies a straightened blowout airstream to the work room; and
a partition plate that causes a horizontal cross-sectional area of a lower portion of the work room to be wider than a horizontal cross-sectional area of an upper portion of the work room, and
wherein the partition plate includes a side partition plate inclined to a side surface of the work room from a position at a predetermined distance down from the blowout straightening plate, and a back partition plate inclined to a back surface of the work room from the position at the predetermined distance down from the blowout straightening plate.

2. The safety cabinet according to claim 1, further comprising:
an airstream partition plate extending downward from the blowout straightening plate in the work room at a predetermined distance from the front shutter.

3. The safety cabinet according to claim 2, wherein the side partition plate and the back partition plate are configured to slide up and down in the work room.

4. The safety cabinet according to claim 2, wherein the side partition plate is inclined to abut the side surface of the work room at an angle of 30 degrees to 45 degrees, and
the back partition plate is inclined to abut the side surface of the work room at an angle of 30 degrees to 45 degrees.

5. The safety cabinet according to claim 2, wherein a lower end of the airstream partition plate is located above a lower end of the front shutter.

6. The safety cabinet according to claim 5, wherein the airstream partition plate suppresses an air speed of a front shutter backside airstream between the airstream partition plate and the front shutter more than an air speed of an airstream of a device installation region in the work room.

7. The safety cabinet according to claim 1, wherein an exhaust slit is provided along a periphery of the device in a workbench which forms a lower surface of the work room, and on which the device is to be installed.

* * * * *